(12) United States Patent
Moussy et al.

(10) Patent No.: US 7,741,335 B2
(45) Date of Patent: *Jun. 22, 2010

(54) USE OF TYROSINE KINASE INHIBITORS FOR TREATING INFLAMMATORY DISEASES

(75) Inventors: Alain Moussy, Paris (FR); Jean Pierre Kinet, Lexington, MA (US)

(73) Assignee: AB Science, Paris (FR)

( * ) Notice: Subject to any disclaimer, the term of this patent is extended or adjusted under 35 U.S.C. 154(b) by 183 days.

This patent is subject to a terminal disclaimer.

(21) Appl. No.: 10/482,039

(22) PCT Filed: Jun. 28, 2002

(86) PCT No.: PCT/IB02/03301

§ 371 (c)(1),
(2), (4) Date: Sep. 7, 2004

(87) PCT Pub. No.: WO03/002108

PCT Pub. Date: Jan. 9, 2003

(65) Prior Publication Data

US 2005/0059688 A1    Mar. 17, 2005

Related U.S. Application Data

(60) Provisional application No. 60/301,410, filed on Jun. 29, 2001.

(51) Int. Cl.
*A61K 31/505* (2006.01)
*A61K 31/517* (2006.01)

(52) U.S. Cl. .................. 514/275; 514/266.1

(58) Field of Classification Search .......... 514/275, 514/266.1
See application file for complete search history.

(56) References Cited

U.S. PATENT DOCUMENTS

| | | | |
|---|---|---|---|
| 3,467,666 A | 9/1969 | Dexter et al. |
| 3,558,653 A | 1/1971 | Coyne et al. |
| 3,725,403 A | 4/1973 | Krapcho |
| 4,587,342 A | 5/1986 | Daluge et al. |
| 5,521,184 A | 5/1996 | Zimmerman |
| 5,639,757 A * | 6/1997 | Dow et al. ............... 514/265.1 |
| 5,792,783 A | 8/1998 | Tang et al. |
| 5,886,020 A | 3/1999 | Tang et al. |
| 5,916,769 A | 6/1999 | Olsen et al. |
| 5,952,374 A | 9/1999 | Clarkson |
| 6,114,371 A | 9/2000 | Tang et al. |
| 6,133,305 A | 10/2000 | Tang et al. |
| 6,235,746 B1 | 5/2001 | Davis et al. |
| 6,420,382 B2 | 7/2002 | Fraley et al. |
| 6,498,165 B1 | 12/2002 | Armstrong et al. |
| 6,498,176 B1 | 12/2002 | Lackey et al. |
| 6,544,988 B1 | 4/2003 | Bilodeau et al. |
| 6,762,180 B1 | 7/2004 | Roth et al. |
| 6,958,335 B2 | 10/2005 | Buchdunger et al. |
| 2002/0010203 A1 * | 1/2002 | Lipson et al. ............... 514/418 |
| 2002/0052386 A1 * | 5/2002 | Armistead et al. .......... 514/269 |
| 2003/0045451 A1 | 3/2003 | Bacus |
| 2003/0091974 A1 | 5/2003 | Moussy et al. |
| 2003/0176443 A1 | 9/2003 | Stein-Gerlach et al. |
| 2004/0028673 A1 | 2/2004 | Netzer et al. |
| 2004/0110810 A1 | 6/2004 | Ciufolini et al. |
| 2004/0241226 A1 | 12/2004 | Moussy et al. |
| 2004/0242601 A1 | 12/2004 | Moussy et al. |
| 2004/0242612 A1 | 12/2004 | Moussy et al. |
| 2004/0259892 A1 | 12/2004 | Moussy et al. |
| 2004/0259893 A1 | 12/2004 | Moussy et al. |
| 2004/0266771 A1 | 12/2004 | Moussy et al. |
| 2004/0266797 A1 | 12/2004 | Moussy et al. |
| 2004/0266801 A1 | 12/2004 | Moussy et al. |
| 2005/0054617 A1 | 3/2005 | Moussy et al. |
| 2005/0059688 A1 | 3/2005 | Moussy et al. |
| 2005/0089838 A1 | 4/2005 | Moussy et al. |
| 2005/0176687 A1 | 8/2005 | Moussy et al. |
| 2005/0222091 A1 | 10/2005 | Moussy et al. |
| 2006/0166281 A1 | 7/2006 | Moussy et al. |
| 2006/0204459 A1 | 9/2006 | Moussy et al. |
| 2006/0275769 A1 | 12/2006 | Moses et al. |

FOREIGN PATENT DOCUMENTS

| | | |
|---|---|---|
| DE | 198 24 922 A | 12/1999 |
| DE | 198 44 003 A | 3/2000 |
| EP | 0 403 238 A2 | 12/1990 |
| EP | 0 564 409 A | 10/1993 |
| EP | 0 586 020 A | 3/1994 |

(Continued)

OTHER PUBLICATIONS bbc.co.uk pp. 1-2.*

(Continued)

*Primary Examiner*—Michael G Hartley
*Assistant Examiner*—Shirley V Gembeh
(74) *Attorney, Agent, or Firm*—Sughrue Mion, PLLC

(57) ABSTRACT

The present invention relates to a method for treating inflammatory diseases such as rheumatoid arthritis (RA), comprising administering a tyrosine kinase inhibitor to a human in need of such treatment, more particularly a non-toxic, selective and potent c-kit inhibitor. Preferably, said inhibitor is unable to promote death of IL-3 dependent cells cultured in presence of IL-3.

1 Claim, 2 Drawing Sheets

FOREIGN PATENT DOCUMENTS

Figure 1A:
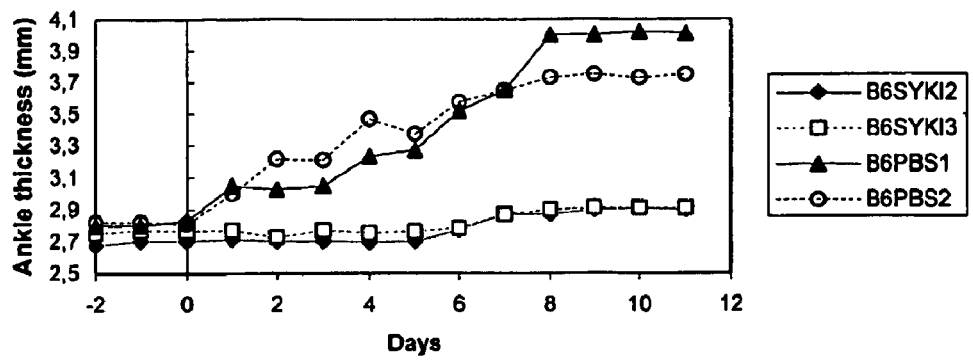

| WO | WO-98/18782 | * | 5/1998 |
|---|---|---|---|
| WO | WO 98 18782 | | 5/1998 |
| WO | WO-9818782 | * | 5/1998 |
| WO | WO 98 35056 A | | 8/1998 |
| WO | WO 98 41525 A | | 9/1998 |
| WO | WO 98 50356 A | | 11/1998 |
| WO | WO 98 55152 A1 | | 12/1998 |
| WO | WO 99 03854 A | | 1/1999 |
| WO | WO-9903854 | * | 1/1999 |
| WO | WO 99 61028 A | | 2/1999 |
| WO | WO 99 11643 A | | 3/1999 |
| WO | WO 99 15500 A | | 4/1999 |
| WO | WO 99 21859 A | | 5/1999 |
| WO | WO 99 61422 A | | 12/1999 |
| WO | WO 99 65908 A | | 12/1999 |
| WO | WO 00 09098 A | | 2/2000 |
| WO | WO 00 40971 A | | 7/2000 |
| WO | WO 00 55139 A | | 9/2000 |
| WO | WO 00 56709 A | | 9/2000 |
| WO | WO 00 67794 A | | 11/2000 |
| WO | WO 00 73297 A | | 12/2000 |
| WO | WO 01 16130 A | | 3/2001 |
| WO | WO 01 27081 A1 | | 4/2001 |
| WO | WO 01 45689 A | | 6/2001 |
| WO | WO 01 47517 A | | 7/2001 |
| WO | WO 01 47950 A | | 7/2001 |
| WO | WO 01 49287 A | | 7/2001 |
| WO | 0164674 A1 | | 9/2001 |
| WO | WO 01 90104 A | | 11/2001 |
| WO | WO 02 40486 A | | 5/2002 |
| WO | WO 02 55517 A | | 7/2002 |
| WO | 0280925 A1 | | 10/2002 |
| WO | WO 03 002106 A3 | | 1/2003 |
| WO | WO 03 035049 A2 | | 5/2003 |
| WO | WO 03 035050 A2 | | 5/2003 |
| WO | 03062215 A1 | | 7/2003 |
| WO | 0164200 A2 | | 9/2007 |

OTHER PUBLICATIONS

Arthritis Res. 2000, 2(6):446-450.*
HealingWell.com 11pages.*
Areugi 1992, 41(3);428-433.*
David J. Hele Respir Res 2001, 2:E003 4 pages.*
Topaly et al. (Leukemia 2001) 15, 342-347.*
Mohammadi Moosa et al. "Structures of the tyrosine kinase domain of fibroblast growth factor receptor in complex with inhibitors", Science, vol. 276, No. 5314, 1997, pp. 955-960.
Ma, Y. et al., "Indolinone Derivatives Inhibit Constitutively Activated Kit Mutants and Kill Neoplastic Mast Cells", *Journal Of Investigative Dermatology*, New York, US, vol. 114, No. 2, Feb. 2000, pp. 392-394.
Imokawa, G. "Paracrine cytokine mechanisms of epidermal hyperpigmentation in UVB-melanosis, lentigo senilis and dematofibroma,", *Pigment Cell Research*, 2002, p. 34, vol. 15, Supp. 9.
James M. Grichnik, et al., "The SCF/KIT Pathway Plays a Critical Role in the Control of Normal Human Melanocyte Homeostasis," *The Journal of Investigative Dermatology*, vol. III, No. 2, pp. 233-238, Aug. 1998, XP001133837.
Hachiya, A. et al., "The inhibitory effect of an extract of clove," *Journal of Investigative Dermatology*, Jul. 2002, p. 341, vol. 19, No. 1.
Hattori, H. et al., "The role of the epidermal stem cell factor (SCF)/c-kit cascade in the hyperpigmentation mechanism of lentigo senilis (LS)," *Pigment Cell Research*, 2002, p. 58, vol. 15, Supp. 9.
A. D. Laird et al, "SU6668 Is a Potent Antiangiogenic and Antitumor Agent that Induces Regression of Established Tumors", *Cancer Research*, vol. 60, pp. 4152-4160, 2000.
B. Smolich et al, "The antiangiogenic protein kinase inhibitors SU5416 and SU6668 inhibit the SCF receptor (c-kit) in a human myeloid leukemia cell line and in acute myeloid leukemia blasts", *Blood*, vol. 97, No. 5, pp. 1413-1421, 2001, XP002229742.
Sinha et al., "Implications for Src Kinases in Hematopoiesis: Signal Transduction Therapeutics", *Journal of Hematotherapy & Stem Cell Research*, vol. 8, pp. 465-480, 1999.
Sinha and Corey, *Signal Transduction Therapeutics*, pp. 471-480, 1999.
Asthma and Bone Health, *NIHORBD-NRC Fact Sheets*, 4 pages, Dec. 2005.
J. Lesinski, "Preventing Bone Loss", The Connection Newspapers, pp. 1-2, May 28, 2003.
www.hopkinsmedicine.org, Bone Loss from Chemotherapy, *Journal of Clinical Oncology*, vol. 19(14); pp. 3306-3311, 2001.
Dolan et al., Rheumatology 41, www.rheumatology.oxfordjournals.org, pp. 1047-1051, 2002.
NIH Osteoporosis and Related Bone Diseases-National Resource Center, "What People With Inflammatory Bowel Disease Need to Know About Osteoporosis", pp. 1-4, updated Feb. 2005.
Krystal G W, et al., "Indolonone Tyrosine Kinase Inhibitors Block Kit Activation and Growth of Small Cell Lung Cancer Cells", vol. 61, No. 9, May 1, 2001, pp. 3660-3668.
Moosa, Mohammadi et al, "Structures of the Tyrosine Kinase Domain of Fibroblast Growth Factor Receptor in Complex with Inhibitors", *Science*, vol. 276, No. 5314, pp. 955-960, 1997.
Defazio, et al., "Interferon β-1a downregulates TNF α-induced intercellular adhesion molecule 1 expression on brain microvascular endothelial cells through a tyrosine kinase-dependent pathway", *Brain research*, vol. 881 (2): pp. 227-230, 2000.
J. Topaly, et al., Synergistic activity of the new ABL-specific tyrosine kinase inhibitor STI571 and chemotherapeutic drugs on BCR-ABL-positive chronic myelogenous leukemia cells, *Leukemia*, vol. 15, pp. 342-347, 2001.
www.gsdl.com, "Laboratory Assessments: IBD and Allergies," GDSL Inflammatory Bowel Disease (IBD) and Allergies, 2 pages, Dec. 2005.
www.health.ucsd.edu, "Researchers Show Beneficial Role of Bacterial DNA in Fighting Inflammatory Bowel Disease," UCSD School of Medicine News Health Sciences Communications, 2 pages, Apr. 2002.
J. Jahnsen, et al., "Bone mineral density in patients with inflammatory bowel disease: a population-based prospective two-year follow-up study", Scand. J. Gastroenterol. Feb. 2004; 39(2), abstract only.
H. Mielants, et al., "Course of gut inflammation in spondylarthropathies and therapeutic consequences," Bailliers Clin. Rheumatol. Feb. 1996; 10(1): abstract only.
A. Yamataka, et al., Localization of Intestinal Pacemaker Cells and Synapses in the Muscle Layers of a Patient with Colonic Hypoganglionosis, *Journal of Pediatric Surgery*, vol. 31, No. 4, pp. 584-587, 1996.
A. Yamataka, et al., A Lack of Intestinal Pacemaker (c-kit) in Aganalionic Bowel of Patients with Hirschsprung's Disease, *Journal of Pediatric Surgery*, vol. 30, No. 3, pp. 441-444, 1995.
C. Njeh, et al, "Bone Loss: Quantitative imaging techniques for asses mass in rheumatoid arthritis", www.pubmedcentral, 9 pages, Dec. 2005.
R. Hicks, "Rheumatoid Arthritis", www.bbc.co.uk, 2 pages, Dec. 2005.
Healingwell.com, "Inflammatory Bowel Disease", www.healingwell.com, 11 pages, Dec. 2005.
Tada S, et al., "The significance of soluble IL-2 receptors in rheumatoid arthritis with interstitial pneumonia", *Aerugi*, vol. 41(3); pp. 428-433, 1992.
Adel A. El-Gendy et al.: Synthesis and Antimicrobial Actibity of Some New 2-indolinone derived ozimes and spiro-isoxazolines.: *Archives of Pharmacal Research (Seoul)*, vol. 23, No. 4, Aug. 2000, pp. 310-314, XP008014265; ISSN: 0253-6269.
A K S Gupta, et al.: "Synthesis of Some New Indolinone Derived hydrazones as Possible, Anti Bacterial Agents", *European Journal of Medicinal Chemistry*, vol. 18, No. 2, 1983, pp. 181-184, XP001109724; ISSN: 0223-5234.
S P Singh, et al.: "Indolinone Derivatives as Potential Antimicrobilal Agents" *Zentralblatt Fuer Mikrobiologie*, vol. 144, No. 2, 1989, pp. 105-109, XP008014264; ISSN: 0232-4393.

Marcus Maurer et al.: "The C-kit Ligand, Stem Cell Factor, can enhance innate immunity through effects on mast cells." *Journal of Experimental Medicine*, vol. 188, No. 12, Dec. 21, 1998, pp. 2343-2348, XP008014256; ISSN: 0022-1007.

Gary R. Klimpoel et al.: "A Role for Stem Cell Factor (SCF): C-kit Interaction(s) in the Intestinal Tract Response to Salmonell Typhimurium Infection.." *Journal of Experimental Medicine*, vol. 184, No. 1, 1996, pp. 271-276, XP008014258, ISSN: 0022-1007.

Andrea Koinig et al.: "Downregulation of C-kit Expression in Human Endotherlial Cells by Inflammatory Stimuli." *Blood*, vol.. 90, No. 1, 1997, pp. 148-155, XP001148729, ISSN: 0006-4971.

Stephen J. Galli et al.: "Mast Cells as Sentinels of Innate Immunity." *Current Opinion in Immunology*, vol. 11, No. 1, Feb. 1999, pp. 53-59, XP004257657, ISSN: 0952-7915.

Medicine House, "Inflammatory Pain Syndromes Arthritis", www.medicinehouse.com, 13 pages, Jan. 2006.

D. Hollander, "Interstital Cystitis and Silk Allergy", *Med. Hypotheses*, vol. 43, pp. 155-156, 1994.

T. Maher et al., "Arthritis Rhinitis: Nothing to Sneeze At", Massachusetts College of Pharmacy and Health Sciences Continuing Education pp. 1-23, Jun. 2002.

D. Hele, "New approaches to modulation of inflammatory processes in airway disease models", *Respiratory research*, vol. 2, No. 5, 4 pages, 2001.

C. Oetzel, et al., The Tyrosine Kinase Inhibitor CGP 57148 (STI 571) Induces Apoptosis in BCR-ABL-positive Cells By Down-Regulating BCL-X, *Clin. Cancer Research*, vol. 6, pp. 1958-1968, 2000.

M. Carroll et al., "CGP 57148, a Tyrosine Kinase Inhibitor, Inhibits the Growth of Cells Expressing BCR-ABL, TEL-ABL and TEL-PDGFR Fusion Proteins" *Blood*, vol. 90, No. 12, pp. 4947-4952, 1997.

P. Ferrao, Expression of Constitutively Activated Human c-Kit in Myb Transformed Early Myeloid Cells Leads to Factor Independence, Histiocytic Differentiation, and Tumorigencity, *Blood*, vol. 90, No. 11, pp. 4569-4552, 1997.

M. Heinrich, "Inhibition of c-kit receptor tyrosine kinase activity by STI-571, a selective tyrosine kinase inhibitor", *Blood*, vol. 96, No. 3, pp. 925-932, 2000, XP001097629.

G. Bold, "New Anilinophthalazines as Potent and Orally Well Absorbed Inhibitors of the VEGF Receptor Tyrosine Kinases Useful as Antagonists of Tumor-Driven Angiogenesis", *J. Med. Chem*, vol. 43, pp. 2310-2323, 2000, XP000971347.

P. Traxler, "Protein tyrosine kinase inhibitors in cancer treatment", *Exp. Opin. Ther. Patents*, vol. 7, No. 6, pp. 571-585, XP002122590, 1997.

Srinivasan, Radhika, Interstital Cystitis Association, "Inflammatory Bowel Disease", www.ichelp.com, 2 pages, Jan. 2006.

R. Saban, "Mast cell regulation of inflammation and gene expression during antigen-induced bladder inflammation in mice", *Physiol Genomics*, vol. 7, pp. 35-43, 2001, XP001161208.

H. Nechustan, et al., Regulation of mast cell growth and proliferation, *Clin. Reviews in Oncology*, vol. 23, pp. 131-150, 1996, XP008019233.

J. Wood et al., "PTK787/Zk 222584, a Novel and Potent Inhibitor of Vascular Endothelial Growth Factor Receptor Tyrosine Kinases, Impairs Vascular Endothelial Growth Factor induced Responses and Tumor Growth after Oral Administration", *Cancer Research*, vol. 60, pp. 2178-2189, 2000, XP000971163.

Petranel Ferrao et al., "Expression of Constitutively Activated Human c-Kit in MyB Transformed Early Myeloid Cells Leads to Factor Independence, Histiocytic Differentiation, and Tumorigenicity", Blood, vol. 90, No. 11, pp. 4539-4552, Dec. 1, 1997.

Longley, B.J., et al., "New Approaches to Therapy for Mastocytosis a Case for Treatment with Kit Kinase Inhibitors", Hematology-Oncology Clinics of North America, W.B. Saunders, U.S., vol. 14, No. 3, Jun. 2000, pp. 689-695.

Marya F. McCarty, et al., "Overexpression of PDGF-BB decreases colorectal and pancreatic cancer growth by increasing tumor pericyte content", The Journal of Clinical Investigation, 2007, 117(8): 2114-2122.

S. P. Singh et al.: "Synthesis of some new 5 Bromo-3-Arylthiosemicarbazone-2-Indolinones as Antimicrobial Agents" *ACTA Pharmaceutica Jugoslavica*, vol. 36, No. 1, pp. 19-26, XP008014269; ISSN: 0001-6667 (1986).

S. Wilkinson et al, "Selective tyrosine kinase inhibitors", *Emerging Drugs*, vol. 5, No. 3, pp. 287-297, XP001062304 (2000).

Hachiya, A. et al., "The inhibitory effect of an extract of clove," *Journal of Investigative Dermatology*, Jul. 2002, p. 341, vol. 119, No. 1.

Notice of Appeal filed Dec. 5, 2008, in U.S. Appl. No. 10/482,039.
Notice of Appeal filed Dec. 11, 2008 in U.S. Appl. No. 10/482,033.
1.111 Amendment filed Dec. 17, 2008, in U.S. Appl. No. 10/482,758.
1.111 Amendment filed Dec. 17, 2008, in U.S. Appl. No. 10/482,037.
Final Office Action dated Jan. 22, 2009, in U.S. Appl. No. 10/490,287.

Dean D. Metcalfe et al., "Mast Cells", Physiological Reviews, 1997, 77(4): 1033-1064.

Final Office Action dated Jan. 12, 2009, in U.S. Appl. No. 10/490,348.

M.A. Golstein et al., "Chronic Interstitial Cystitis Occurring during the Shift between Rheumatoid Arthritis and Lupus", Clinical Rheumatology, 1994, 13(1): 119-122.

B. Foxwell et al., "Prospects for the development of small molecular weight compounds to replace anti-tumour necrosis factor biological agents", Ann Rheum Dis, 2003, 62 (Suppl. II): ii90-ii93.

Akira Inoue et al., "Suppression of surfactant protein A by an epidermal growth factor receptor tyrosine kinase inhibitor exacerbates lung inflammation", Cancer Sci., 2008, 99(8): 1679-1684.

Peter Traxler, "Tyrosine kinases as targets in cancer therapy- successes and failures", Expert Opin. Ther. Targets, 2003, 7(2): 215-234.

Fahad A. Al-Obeidi et al., "Development of inhibitors for protein tyrosine kinases", Oncogene, 2000, 19: 5690-5701.

1.116 Amendment filed Jan. 30, 2009 in U.S. Appl. No. 10/490,348.
Carsten Oetzel et al., "The Tyrosine Kinase Inhibitor CGP 57148 (ST1 571) Induces Apoptosis in BCR-ABL-positive Cells by Down-Regulating BCL-X", Clinical Cancer Research, 2000, 6: 1958-1968.

A. Douglas Laird et al., "SU6668 Is A Potent Antiangiogenic and Antitumor Agent that Induces Regression of Established Tumors", Cancer Research, 2000, 60: 4152-4160.

Martin Carroll et al., "CGP 57148, A Tyrosine Kinase Inhibitor, Inhibits the Growth of Cells Expressing BCR-ABL, TEL-ABL and TEL-PDGFR Fusion Proteins", Blood, 1997, 90(12): 4947-4952.

Final Office Action dated Nov. 29, 2007 in U.S. Appl. No. 10/482,033.
Final Office Action dated May 16, 2007 in U.S. Appl. No. 10/482,035.
Request for Continued Examination and 1.114 Amendment filed Nov. 16, 2007 in U.S. Appl. No. 10/482,035.

K.F. Chung, et al. British Medical Bulletin, 1992, 48:179-189 (Abstract only).

www.pueblo.gsa.gov/cic_text/health/atopic-dermatitis/defining.html, Jan. 22, 2000.

Notice of Non-Compliant Amendment dated Jul. 11, 2007 in U.S. Appl. No. 10/482,037.
Response to Notice of Non-Compliant Amendment filed Aug. 10, 2007 in U.S. Appl. No. 10/482,037.
Final Office Action dated Nov. 2, 2007 in U.S. Appl. No. 10/482,037.
Request for Continued Examination and 1.114 Amendment filed Mar. 3, 2008 in U.S. Appl. No. 10/482,037.
Final Office Action dated Oct. 3, 2007 in U.S. Appl. No. 10/482,039.
1.111 Amendment filed Feb. 19, 2008 in U.S. Appl. No. 10/482,177.
Final Office Action dated May 29, 2008 in U.S. Appl. No. 10/482,177.

Wei Zhang et al., "Modulation of Tumor Angiogenesis by Stem Cell Factor", Cancer Research, 2000, 60: 6757-6762.

Restriction and Election of Species Requirements dated Oct. 15, 2007 in U.S. Appl. No. 10/482,758.
Response to Restriction and Election of Species Requirements filed Mar. 14, 2008 in U.S. Appl. No. 10/482,758.
Restriction Requirement dated Oct. 2, 2007 in U.S. Appl. No. 10/490,287.
Response to Restriction Requirement filed Jan. 2, 2008 in U.S. Appl. No. 10/490,287.
Non-Final Office Action dated Mar. 18, 2008 in U.S. Appl. No. 10/490,287.

Frederic Feger et al., "The role of mast cells in host defense and their subversion by bacterial pathogens," Trends in Immunology, 2002, 23(3): 151-158.

Mosby's GenRx: The Complete Reference for Generic and Brand Drugs, 1998, pp. II-1991 to II-1994.

1.111 Amendment filed Dec. 4, 2007 in U.S. Appl. No. 10/490,334.

Non-Final Office Action dated Feb. 20, 2008 in U.S. Appl. No. 10/490,334.

1.111 Amendment filed May 20, 2008 in U.S. Appl. No. 10/490,334.

1.111 Amendment filed Dec. 21, 2007 in U.S. Appl. No. 10/490,348.

1.111 Amendment filed Dec. 10, 2007 in U.S. Appl. No. 10/505,842.

Final Office Action dated Mar. 13, 2008 in U.S. Appl. No. 10/505,842.

Request for Continued Examination and 1.114 Response filed Mar. 28, 2008 in U.S. Appl. No. 10/482,033.

Non-Final Office Action dated Jan. 30, 2008 in U.S. Appl. No. 10/482,035.

Non Final Office Action dated Jun. 17, 2008 in U.S. Appl. No. 10/482,758.

Patrick D. W. Kiely et al., "Mercuric Chloride-Induced Vasculitis in the Brown Norway Rat: αβ T Cell-Dependent and -Independent Phases", The Journal of Immunology, 1997, 159:5100-5106.

Non-Final Office Action dated Jun. 17, 2008 in U.S. Appl. No. 10/482,037.

Non-Final Office Action dated Jun. 11, 2008 in U.S. Appl. No. 10/482,033.

Mary B. Edelson et al., "Circulating Pro- and Counterinflammatory Cytokine Levels and Severity in Necrotizing Enterocolitis", Pediatrics, 1999, 103(4): 766-771. (Abstract Only).

Restriction and Election of Species Requirements dated Jun. 9, 2008 in U.S. Appl. No. 10/490,286.

Non-Final Office Action dated Jun. 25, 2008 in U.S. Appl. No. 10/490,348.

F. Aldenborg et al., "Proliferation and transepithelial migration of mucosal mast cells in interstitial cystitis", Immunology, 1986, 58:411-416.

M. Hohenfellner et al., "Interstitial cystitis: increased sympathetic innervation and related neuropeptide synthesis", J. Urol. 1992, 147(3):Abstract Only.

1.111 Response filed Jul. 30, 2008 in U.S. Appl. No. 10/482,035.

1.111 Amendment filed Aug. 18, 2008 in U.S. Appl. No. 10/490,287.

Non-Final Office Action dated Aug. 21, 2006 in U.S. Appl. No. 10/490,334.

Final Office Action dated Oct. 24, 2008 in U.S. Appl. No. 10/482,035.

David A. Walsh et al., "Angiogenesis in the pathogenesis of inflammatory joint and lung diseases", Arthritis Research, 2001, 3(3): 147-153.

Request for Continued Examination and 1.114 Amendment filed Dec. 1, 2008 in U.S. Appl. No. 10/482,177.

1.111 Amendment filed Sep. 25, 2008 in U.S. Appl. No. 10/490,348.

Giovanni Defazio et al., Interferon β-1a downregulates TNFα-induced intercellular adhesion molecule 1 expression on brain microvascular endothelial cells through a tyrosine kinase-dependent pathway', Brain Research, 2000, 881:227-230.

Ariel Fernandez et al., "An anticancer C-Kit kinase inhibitor is reengineered to make it more active and less cardiotoxic", The Journal of Clinical Investigation, 2007, 117(12): 4044-4054.

C. Gelbmann et al., "Strictures in Crohn's disease are characterised by an accumulation of mast cells colocalised with laminin but not with fibronectin or vitronectin", Gut, 1999, 45(2):210-217.

J. Gutknecht et al., "Leukemia and Crohn's Disease", Digestive Diseases and Sciences, 1986, 31(12):1391.

www.hopkinsmedicine.org, Bone Loss from Chemotherapy, *Journal of Clinical Oncology*, vol. 19(14); pp. 3306-3311, 2001.

International Search Report dated Feb. 16, 2004 for International Application No. PCT/1803/01071.

International Search Report dated Sep. 2, 2003 for International Application No. PCT/IB03/01425.

International Search Report dated Feb. 24, 2003 for International Application No. PCT/IB02/03295.

International Search Report dated Jan. 31, 2003 for International Application No. PCT/IB02/03296.

International Search Report dated Mar. 31, 2003 for International Application No. PCT/IB02/03317.

International Search Report dated Nov. 6, 2003 for International Application No. PCT/IB02/04236.

International Search Report dated Jul. 9, 2003 for International Application No. PCT/IB02/04251.

S.H. Mir Madjlessi et al., "Inflammatory bowel disease and leukemia. A report of seven cases of leukemia in ulcerative colitis and Crohn's disease and review of the literature", Dig. Dis. Sci., 1986, 10:1025-1031.

Lee S. Rosen et al., "Phase I Experience with SU6668, a novel Multiple Receptor Tyrosine Kinase Inhibitor in Patients with Advanced Malignancies", Proc Am Soc Clin Oncol, 2001, 20 (Abstract 383).

Peter Vajkoczy et al., "Inhibition of Tumor Growth, Angiogenesis, and Microcirculation by the Novel Flk-1 Inhibitor SU5416 as Assessed by Intravital Multi-fluorescence Videomicroscopy", Neoplasia, 1999, 1(1): 31-41.

Non-final Office Action issued, dated Jan. 6, 2006 in U.S. Appl. No. 10/482,033.

Response to Non-final Office Action filed May 5, 2006 in U.S. Appl. No. 10/482,033.

Non-final Office Action issued, dated Jul. 28, 2006 in U.S. Appl. No. 10/482,033.

Response to Non-final Office Action filed Nov. 28, 2006 in U.S. Appl. No. 10/482,033.

Non-final Office Action issued, dated Apr. 9, 2007 in U.S. Appl. No. 10/482,033.

Response to Non-final Office action filed Sep. 10, 2007 in U.S. Appl. No. 10/482,033.

Request for Continued Examination and 1.114 Response filed Feb. 11, 2009 in U.S. Appl. No. 10/482,033.

Non-Final Office Action mailed Apr. 23, 2009, in U.S. Appl. No. 10/482,033.

Notice of Allowance issued, dated Oct. 27, 2009, in U.S. Appl. No. 10/482,033.

Non-final Office Action issued, dated Jan. 20, 2006 in U.S. Appl. No. 10/482,035.

Response to Non-final Office Action filed Apr. 20, 2006 in U.S. Appl. No. 10/482,035.

Non-final Office Action issued, dated Nov. 2, 2006 in U.S. Appl. No. 10/482,035.

Response to Non-final Office Action filed Feb. 2, 2007 in U.S. Appl. No. 10/482,035.

Request for Continued Examination and 1.114 Response filed Feb. 23, 2009, in U.S. Appl. No. 10/482,035.

Non-Final Office Action mailed Apr. 29, 2009 in U.S. Appl. No. 10/482,035.

Notice of Allowance issued, dated Oct. 23, 2009, in U.S. Appl. No. 10/482,035.

Restriction Requirement issued, dated Sep. 7, 2006 in U.S. Appl. No. 10/482,037.

Response to Restriction Requirement filed Oct. 6, 2006 in U.S. Appl. No. 10/482,037.

Non-Final Office Action issued, dated Dec. 20, 2006 in U.S. Appl. No. 10/482,037.

Response to Non-Final Oa filed Apr. 20, 2007 in U.S. Appl. No. 10/482,037.

Final Office Action mailed Mar. 30, 2009, in U.S. Appl. No. 10/482,037.

Request for Continued Examination and 1.114 Response filed Sep. 30, 2009 in U.S. Appl. No. 10/482,037.

Restriction Requirement issued, dated Mar. 29, 2007 in U.S. Appl. No. 10/482,177.

Response to Restriction Requirement filed May 25, 2007 in U.S. Appl. No. 10482,177.

Non-final Office Action issued, dated Aug. 17, 2007 in U.S. Appl. No. 10482,177.

Non-Final Office Action dated Mar. 3, 2009, in U.S. Appl. No. 10/482,177.

Final Office Action mailed Mar. 4, 2009, in U.S. Appl. No. 10/482,758.

Non-final Office Action issued, dated Jun. 4, 2007 in U.S. Appl. No. 10/490,334.
1.111 Amendment filed Dec. 22, 2008, in U.S. Appl. No. 10/490,334.
Non-Final Office Action mailed Apr. 28, 2009 in U.S. Appl. No. 10/490,334.
Non-final Office Action issued, dated Jan. 18, 2006 in U.S. Appl. No. 10/490,348.
Response to Non-final Office Action filed Apr. 18, 2006 in U.S. Appl. No.10/490,348.
Non-final Office Action issued, dated Jul. 17, 2006 in U.S. Appl. No. 10/490,348.
Response to Non-final Office Action issued, dated Jan. 17, 2007 in U.S. Appl. No. 10/490,348.
Non-final Office Action issued, dated Aug. 22, 2007 in U.S. Appl. No. 10/490,348.
Non-Final Office Action mailed Mar. 19, 2009, in U.S. Appl. No. 10/490,348.
Restriction Requirement issued, dated Apr. 19, 2007 in U.S. Appl. No. 10/505,842.
Response to Restriction Requirement filed Aug. 17, 2007 in U.S. Appl. No. 10/505,842.
Non-final Office Action issued, dated Sep. 10, 2007 in U.S. Appl. No. 10/505,842.
Restriction Requirement mailed Jan. 29, 2009, in U.S. Appl. No. 10/505,899.
Restriction Requirement mailed Jan. 19, 2007 in U.S. Appl. No. 10/523,018.
Restriction Requirement mailed Jan. 30, 2007 in U.S. Appl. No. 10/482,034.
Non-Final Office Action mailed Jan. 3, 2006 in U.S. Appl. No. 10/482,036.
1.111 Amendment filed Mar. 23, 2006 in U.S. Appl. No. 10/482,036.
Non-Final Office Action mailed Jul. 20, 2006 in U.S. Appl. No. 10/482,036.
Restriction Requirement mailed Oct. 21, 2005 in U.S. Appl. No. 10/482,040.
Restriction Requirement mailed Jan. 23, 2007 in U.S. Appl. No. 10/482,179.

* cited by examiner

SEQUENCE LISTING

<160> NUMBER OF SEQ ID NOS: 5

<210> SEQ ID NO 1
<211> LENGTH: 976
<212> TYPE: PRT
<213> ORGANISM: Homo sapiens
<220> FEATURE:
<223> OTHER INFORMATION: Human c-kit

```
<400> SEQUENCE: 1

Met Arg Gly Ala Arg Gly Ala Trp Asp Phe Leu Cys Val Leu Leu
  1               5                  10                  15

Leu Leu Arg Val Gln Thr Gly Ser Ser Gln Pro Ser Val Ser Pro Gly
            20                  25                  30

Glu Pro Ser Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415
```

```
Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
            450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
            725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
            805                 810                 815

Ile Lys Asn Asp Ser Asn Tyr Val Val Lys Gly Asn Ala Arg Leu Pro
            820                 825                 830
```

-continued

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
        850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 2
<211> LENGTH: 30
<212> TYPE: DNA
<213> ORGANISM: Homo sapiens
<220> FEATURE:
<223> OTHER INFORMATION: Primer

<400> SEQUENCE: 2
aagaagagat ggtacctcga ggggtgaccc                                    30

<210> SEQ ID NO 3
<211> LENGTH: 33
<212> TYPE: DNA
<213> ORGANISM: Homo sapiens
<220> FEATURE:
<223> OTHER INFORMATION: Primer

<400> SEQUENCE: 3
ctgcttcgcg gccgcgttaa ctcttctcaa cca                                33

<210> SEQ ID NO 4
<211> LENGTH: 20
<212> TYPE: DNA
<213> ORGANISM: Homo sapiens
<220> FEATURE:
<223> OTHER INFORMATION: Primer

<400> SEQUENCE: 4
agctcgttta gtgaaccgtc                                               20

<210> SEQ ID NO 5
<211> LENGTH: 20
<212> TYPE: DNA
<213> ORGANISM: Homo sapiens
<220> FEATURE:
<223> OTHER INFORMATION: Primer

<400> SEQUENCE: 5
gtcagacaaa atgatgcaac                                               20

USE OF TYROSINE KINASE INHIBITORS FOR TREATING INFLAMMATORY DISEASES

This application claims benefit to U.S. Provisional Application 60/301,410 filed Jun. 29, 2001.

The present invention relates to a method for treating inflammatory diseases such as rheumatoid arthritis (RA), comprising administering a tyrosine kinase inhibitor to a human in need of such treatment, more particularly a non-toxic, selective and potent c-kit inhibitor. Preferably, said inhibitor is unable to promote death of IL-3 dependent cells cultured in presence of IL-3.

Millions of people are afflicted with rheumatoid arthritis in the USA alone, which represent approximately 1% of the total adult population (Mitchell, D. 1985. Rheumatoid Arthritis, eds. J. B. Lippincott Co., Philadelphia, pp. 133-150). This progressive inflammatory disease is very important both socially and economically because it leads to the disabling and extensive suffering of individuals. The distribution of affected and deformed joints typically involves the small articulations of the hands and feet, although the larger appendicular joints like the shoulders and hips are often affected in established disease.

Current methods for treating rheumatoid arthritis include administration of non-steroidal anti-inflammatory drugs such as acetylsalicylic acid (aspirin), ibuprofen, naproxen, cox2 inhibitors and other agents such as penicillamine, methotrexate, cytotoxic agents (e.g., azothrioprine), 4-aminoquinoline agents, and immunomodulators. However, no satisfactory treatment is available as of today. In addition, many of the therapeutic agents administered to alleviate pain and inflammation associated with the disease, such as disease-modifying antirheumatic drugs (DMARDs) and non-steroidal anti-inflammatory agents (NSAIDs), produce intolerable side effects. The use of nonspecific immunosuppressive drugs which suppress the entire immune system has also been proposed but it increases the risk of infection. Furthermore, prolonged use of such drugs can entail severe toxic side effects and is only partially effective in mitigating symptoms of rheumatoid arthritis.

Therefore, improved treatments of rheumatoid arthritis, which can suppress symptoms such as inflammation, swelling, abnormal neovascularization, bone erosion, or cartilage erosion are needed.

The cause of rheumatoid arthritis remains elusive but it is now generally accepted that infectious agents or toxins, genetic susceptibility, and immune or autoimmune responses play direct or indirect roles. After initiation of the disease process, it is believed that activated T cells and their products are responsible for the progressive destruction of articular cartilage and sub-chondral bone that is characteristic of rheumatoid arthritis.

The symptoms of the disease result from a massive increase in the number of cells lining the synovium of the joint. The various cell types which are present include type A synoviocytes, which have the characteristics of monocytes or terminally differentiated macrophages, and type B synoviocytes which are fibroblast-like. As these cells increase in number, the continuous inflammation causes initial symptoms. Eventually, local release of enzymes by the synovial internal lining degrade the extracellular matrix and cause deformity. Panayi et al, 1992, Arth. Rheum., 35, pp.729-735 mentioned that rheumatoid factors is caused by a cell-mediated process involving T cells, antigen-presenting cells (APC), macrophages, synoviocytes, and cytokines. T cells (Panayi et al., 1992, Arthritis Rheum. 35, 729-735), B cells (Zvaifler, 1973, Adv. Immunol. 265, 265-336), and other leukocytes such as dendritic cells, macrophages and neutrophils (Thomas and Lipsky, 1996, Arthritis Rheum. 39, 183-190) have been shown to play a role the pathogenesis of this inflammatory disease. Rheumatoid arthritis is also generally considered an autoimmune disease that is thought to be associated with activity of autoreactive T cells (Harris E., 1990, The New England Journal of Medicine, 322: 1277-1289).

Cytokines have also been indicated as being implicated in the pathophysiology of rheumatoid arthritis. Tumor necrosis factor (TNF-a) has received attention because it is consistently found in synovium of patients suffering from rheumatoid arthritis. In addition, anti-human TNF was demonstrated to prevent the development of arthritis in a transgenic human TNF-a mouse model. Elliott et al. (Arthritis Rheum. 1993, 36, 1681-1690) used chimeric (mouse-human) antibodies to TNF-a to treat patients with active rheumatoid arthritis. But, TNF-a might not be the only factor responsible for this inflammatory disease.

Therefore, there is a need for alternative treatments of these diseases that would be more effective on the long term in regards to the above mentioned observations and which would be well tolerated especially in respect to repeated administration.

In connection with the invention, we examined the distribution of mast cell subsets and their density in synovium from normal subjects and from patients with rheumatoid arthritis (RA). In normal synovium, the majority of mast cells belongs to the MCTC subset, outnumbering MCT cells by 5:1. The mean density of mast cells was significantly increased in RA synovia compared with normal synovia. In RA, both subsets expanded and were associated with infiltrating inflammatory cells or with regions of highly cellular fibrous tissue (mainly MCTC). In addition, a correlation was observed between clinical parameters of activity or progression of rheumatoid disease and the density of MCTC cells, especially the density in the superficial layer of synovium.

As a result, MCTC mast cells expand in RA, associate with regions of "active" fibrosis, and correlate with parameters of disease activity or progression of RA. These findings implicate the MCTC subset of mast cells in the pathologic mechanisms that mediate tissue damage in RA.

Mast cells (MC) are tissue elements derived from a particular subset of hematopoietic stem cells that express CD34, c-kit and CD13 antigens (Kirshenbaum et al, Blood. 94: 2333-2342, 1999 and Ishizaka et al, Curr Opin Immunol. 5: 937-43, 1993). Immature MC progenitors circulate in the bloodstream and differentiate in tissues. These differentiation and proliferation processes are under the influence of cytokines, one of utmost importance being Stem Cell Factor (SCF), also termed Kit ligand (KL), Steel factor (SL) or Mast Cell Growth Factor (MCGF). SCF receptor is encoded by the protooncogene c-kit, that belongs to type III receptor tyrosine kinase subfamily (Boissan and Arock, J Leukoc Biol. 67: 13548, 2000). This receptor is also expressed on others hematopoietic or non hematopoietic cells. Ligation of c-kit receptor by SCF induces its dimerization followed by its transphosphorylation, leading to the recruitement and activation of various intracytoplasmic substrates. These activated substrates induce multiple intracellular signaling pathways responsible for cell proliferation and activation (Boissan and Arock, 2000). Mast cells are characterized by their heterogeneity, not only regarding tissue location and structure but also at the functional and histochemical levels (Aldenborg and Enerback., Histochem. J. 26: 587-96, 1994; Bradding et al. J. Immunol. 155: 297-307, 1995; Irani et al, J. Immunol. 147: 247-53, 1991; Miller et al, Curr Opin Immunol. 1: 637-42, 1989 and Welle et al, J Leukoc Biol. 61: 233-45, 1997).

In connection with the invention, it is proposed that mast cells play a crucial role in the pathogenesis of inflammatory diseases associated with mast cells, such as rheumatoid arthritis, conjunctivitis, rheumatoid spondylitis, osteoarthritis, gouty arthritis and other arthritic conditions, in that they produce a large variety of mediators categorized here into three groups:

preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-a, GM-CSF, MIP-1a, MIP-1b and IFN-γ).

Then, liberation by activated mast cells of mediators (TNF-a, leucotrienes, prostaglandines etc. . . . ) can induce these inflammatory diseases. In addition, mast cells activatie T cells and macrophages, which further contributes to the inflammation and destruction process observed for example in rheumatoid arthritis.

Therefore, the invention provides a new therapeutic strategy aimed at blocking the activation of mast cells involved in RA.

In U.S. Pat. No. 6,211,228, tryptase inhibitors are proposed for the prevention and treatment of mast-cell mediated inflammatory disorders and in U.S. Pat. No. 5,861,264 anti-tryptase detection is used as a diagnostic for inflammatory diseases. However, decreasing the activity of free tryptase released by activated mast cells is not sufficient to block chain reactions caused by the others mast cells released factors mentioned above.

In contrast, the present invention proposes to use c-kit specific kinase inhibitors to inhibit mast cell proliferation, survival and activation. A new route for treating inflammatory diseases is provided, which consists of destroying mast cells playing a role in the pathogenesis of these disorders. It has been found that tyrosine kinase inhibitors and more particularly c-kit inhibitors are especially suited to reach this goal.

DESCRIPTION

The present invention relates to a method for treating inflammatory diseases comprising administering a tyrosine kinase inhibitor to a mammal in need of such treatment.

Tyrosine kinase inhibitors are selected for example from bis monocyclic, bicyclic or heterocyclic aryl compounds (WO 92/20642), vinylene-azaindole derivatives (WO 94/14808) and 1-cyclopropyl-4-pyridyl-quinolones (U.S. Pat. No. 5,330,992), Styryl compounds (U.S. Pat. No. 5,217,999), styryl-substituted pyridyl compounds (U.S. Pat. No. 5,302,606), seleoindoles and selenides (WO 94/03427), tricyclic polyhydroxylic compounds (WO 92/21660) and benzylphosphonic acid compounds (WO 91/15495), pyrimidine derivatives (U.S. Pat. No. 5,521,184 and WO 99/03854), indolinone derivatives and pyrrol-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940) and aryl and heteroaryl quinazoline (U.S. Pat. No. 5,721,237, U.S. Pat. No. 5,714,493, U.S. Pat. No. 5,710,158 and WO 95/15758).

Preferably, said tyrosine kinase inhibitors are unable to promote death of IL-3 dependent cells cultured in presence of IL-3.

In another embodiment, the invention is directed to a method for treating inflammatory diseases comprising administering a c-kit inhibitor to a mammal in need of such treatment.

Preferably, said c-kit inhibitor is a non-toxic, selective and potent c-kit inhibitor. Such inhibitors can be selected from the group consisting of indolinones, pyrimidine derivatives, pyrrolopyrimidine derivatives, quinazoline derivatives, quinoxaline derivatives, pyrazoles derivatives, bis monocyclic, bicyclic or heterocyclic aryl compounds, vinylene-azaindole derivatives and pyridyl-quinolones derivatives, styryl compounds, styryl-substituted pyridyl compounds, seleoindoles, selenides, tricyclic polyhydroxylic compounds and benzylphosphonic acid compounds.

Among preferred compounds, it is of interest to focus on pyrimidine derivatives such as N-phenyl-2-pyrimidine-amine derivatives (U.S. Pat. No. 5,521,184 and WO 99/03854), indolinone derivatives and pyrrol-substituted indolinones (U.S. Pat. No. 5,792,783, EP 934 931, U.S. Pat. No. 5,834,504), U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343,940), 4-amino-substituted quinazolines (U.S. Pat. No. 3,470,182), 4-thienyl-2-(1H)-quinazolones, 6,7-dialkoxyquinazolines (U.S. Pat. No. 3,800,039), aryl and heteroaryl quinazoline (U.S. Pat. No. 5,721,237, U.S. Pat. No. 5,714,493, U.S. Pat. No. 5,710,158 and WO 95/15758), 4-anilinoquinazoline compounds (U.S. Pat. No. 4,464,375), and 4-thienyl-2-(1H)-quinazolones (U.S. Pat. No. 3,551,427).

So, preferably, the invention relates to a method for treating inflammatory diseases comprising administering a non toxic, potent and selective c-kit inhibitor. Such inhibitor can be selected from pyrimidine derivatives, more particularly N-phenyl-2-pyrimidine-amine derivatives of formula 1:

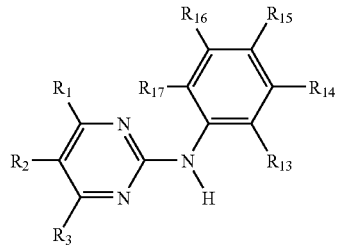

wherein the R1, R2, R3, R13 to R17 groups have the meanings depicted in EP 564 409 B1, incorporated herein in the description.

Preferably, the N-phenyl-2-pyrimidine-amine derivative is selected from the compounds corresponding to formula II:

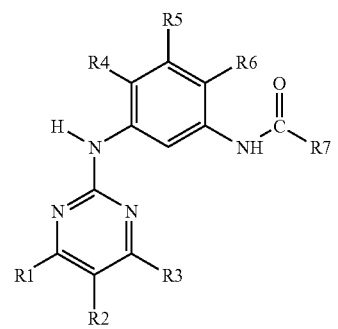

Wherein R1, R2 and R3 are independently chosen from H, F, Cl, Br, I, a C1-C5 alkyl or a cyclic or heterocyclic group, especially a pyridyl group;

R4, R5 and R6 are independently chosen from H, F, Cl, Br, I, a C1-C5 alkyl, especially a methyl group;

and R7 is a phenyl group bearing at least one substituent, which in turn possesses at least one basic site, such as an amino function.

Preferably, R7 is the following group:

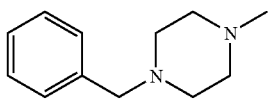

Among these compounds, the preferred are defined as follows:

R1 is a heterocyclic group, especially a pyridyl group,

R2 and R3 are H,

R4 is a C1-C3 alkyl, especially a methyl group,

R5 and R6 are H, and R7 is a phenyl group bearing at least one substituent, which in turn possesses at least one basic site, such as an amino function, for example the group:

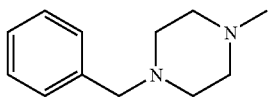

Therefore, in a preferred embodiment, the invention relates to a method for treating inflammatory diseases comprising the administration of an effective amount of the compound known in the art as CGP57148B:

4-(4-méthylpipérazine-1-ylméthyl)-N-[4-méthyl-3-[(4-pyridine-3-yl)pyrimidine-2 yl)amino]phényl]-benzamide corresponding to the following formula:

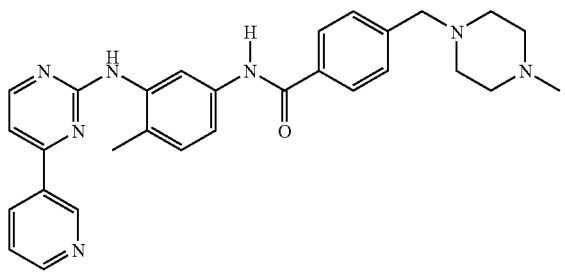

The preparation of this compound is described in example 21 of EP 564 409 and the β-form, which is particularly useful is described in WO 99/03854.

Alternatively, the c-kit inhibitor can be selected from:

indolinone derivatives, more particularly pyrrol-substituted indolinones, monocyclic, bicyclic aryl and heteroaryl compounds, quinazoline derivatives, and quinoxalines, such as 2-phényl-quinoxaline derivatives, for example 2-phenyl-6,7-dimethoxy quinoxaline.

In a preferred aspect, the invention contemplated the method mentioned above, wherein said c-kit inhibitor is unable to promote death of IL-3 dependent cells cultured in presence of IL-3.

The expression "inflammatory diseases" refers herein to inflammatory diseases associated with mast cells, such as rheumatoid arthritis, conjunctivitis, rheumatoid spondylitis, osteoarthritis, gouty arthritis and other arthritic conditions, which are embraced by the invention.

In a further embodiment, c-kit inhibitors as mentioned above are inhibitors of activated c-kit. In frame with the invention, the expression "activated c-kit" means a constitutively activated-mutant c-kit including at least one mutation selected from point mutations, deletions, insertions, but also modifications and alterations of the natural c-kit sequence (SEQ ID No1). Such mutations, deletions, insertions, modifications and alterations can occur in the transphosphorylase domain, in the juxtamembrane domain as well as in any domain directly or indirectly responsible for c-kit activity. The expression "activated c-kit" also means herein SCF-activated c-kit. Preferred and optimal SCF concentrations for activating c-kit are comprised between $5.10^{-7}$ M and $5.10^{-6}$ M, preferably around $2.10^{-6}$ M. In a preferred embodiment, the activated-mutant c-kit in step a) has at least one mutation proximal to Y823, more particularly between amino acids 800 to 850 of SEQ ID No1 involved in c-kit autophosphorylation, notably the D816V, D816Y, D816F and D820G mutants. In another preferred embodiment, the activated-mutant c-kit in step a) has a deletion in the juxtamembrane domain of c-kit. Such a deletion is for example between codon 573 and 579 called c-kit d(573-579). The point mutation V559G proximal to the juxtamembrane domain c-kit is also of interest.

In this regard, the invention contemplates a method for treating inflammatory diseases comprising administering to a mammal in need of such treatment a compound that is a selective, potent and non toxic inhibitor of activated c-kit obtainable by a screening method which comprises:

a) bringing into contact (i) activated c-kit and (ii) at least one compound to be tested; under conditions allowing the components (i) and (ii) to form a complex, b) selecting compounds that inhibit activated c-kit, c) testing and selecting a subset of compounds identified in step b), which are unable to promote death of IL-3 dependent cells cultured in presence of IL-3.

This screening method can further comprise the step consisting of testing and selecting a subset of compounds identified in step b) that are inhibitors of mutant activated c-kit (for example in the transphosphorylase domain), which are also capable of inhibiting SCF-activated c-kit wild.

Alternatively, in step a) activated c-kit is SCF-activated c-kit wild.

A best mode for practicing this method consists of testing putative inhibitors at a concentration above 10 µM in step a). Relevant concentrations are for example 10, 15, 20, 25, 30, 35 or 40 µM.

In step c), IL-3 is preferably present in the culture media of IL-3 dependent cells at a concentration comprised between 0.5 and 10 ng/ml, preferably between 1 to 5 ng/ml.

Examples of IL-3 dependent cells include but are not limited to:

cell lines naturally expressing and depending on c-kit for growth and survival. Among such cells, human mast cell lines can be established using the following procedures:

normal human mast cells can be infected by retroviral vectors containing sequences coding for a mutant c-kit comprising the c-kit signal peptide and a TAG sequence allowing to differentiate mutant c-kits from c-kit wild expressed in hematopoetic cells by means of antibodies.

This technique is advantageous because it does not induce cellular mortality and the genetic transfer is stable and gives satisfactory yields (around 20%). Pure normal human mast cells can be routinely obtained by culturing precursor cells originating from blood obtained from human umbilical vein. In this regard, heparinated blood from umbilical vein is centrifuged on a Ficoll gradient so as to isolate mononucleated cells from other blood components. CD34+ precursor cells are then purified from the isolated cells mentioned above using the immunomagnetic selection system MACS (Miltenyi biotech). CD34+ cells are then cultured at 37° C. in 5% $CO_2$ atmosphere at a concentration of $10^5$ cells per ml in the medium MCCM (α-MEM supplemented with L-glutamine, penicillin, streptomycin, 5 $10^{-5}$ M β-mercaptoethanol, 20% veal faetal serum, 1% bovine albumin serum and 100 ng/ml recombinant human SCF. The medium is changed every 5 to 7 days. The percentage of mast cells present in the culture is assessed each week, using May-Grünwal Giemsa or Toluidine blue coloration. Anti-tryptase antibodies can also be used to detect mast cells in culture. After 10 weeks of culture, a pure cellular population of mast cells (>98%) is obtained.

It is possible using standard procedures to prepare vectors expressing c-kit for transfecting the cell lines established as mentioned above. The cDNA of human c-kit has been described in Yarden et al., (1987) EMBO J.6 (11), 3341-3351. The coding part of c-kit (3000 bp) can be amplified by PCR and cloned, using the following oligonucleotides:

```
sens
5'AAGAAGAGATGGTACCTCGAGGGGTGACCC3'      (SEQ ID No 2)

antisens
5'CTGCTTCGCGGCCGCGTTAACTCTTCTCAACCA3'  (SEQ ID No 3)
```

The PCR products, digested with Not1 and Xho1, has been inserted using T4 ligase in the pFlag-CMV vector (SIGMA), which vector is digested with Not1 and Xho1 and dephosphorylated using CIP (Biolabs). The pFlag-CMV-c-kit is used to transform bacterial clone XL1-blue. The transformation of clones is verified using the following primers:

```
    sens
    5'AGCTCGTTTAGTGAACCGTC3',    (SEQ ID No 4)

antisens
    5'GTCAGACAAAATGATGCAAC3'.    (SEQ ID No 5)
```

Directed mutagenesis is performed using relevant cassettes is performed with routine and common procedure known in the art.

The vector Migr-1 (ABC) can be used as a basis for constructing retroviral vectors used for transfecting mature mast cells. This vector is advantageous because it contains the sequence coding for GFP at the 3' and of an IRES. These features allow to select cells infected by the retrovirus using direct analysis with a fluorocytometer. As mentioned above, the N-terminal sequence of c-kit c-DNA can be modified so as to introduce a Flag sequence that will be useful to discriminating heterogeneous from endogenous c-kit.

Other IL-3 dependent cell lines that can be used include but are not limited to:

BaF3 mouse cells expressing wild-type or mutated form of c-kit (in the juxtamembrane and in the catalytic sites) are described in Kitayama et al, (1996), Blood 88, 995-1004 and Tsujimura et al, (1999), Blood 93, 1319-1329.

IC-2 mouse cells expressing either c-kit$^{WT}$ or c-kit$^{D814Y}$ are presented in Piao et al, (1996), Proc. Natl. Acad. Sci. USA 93, 14665-14669.

IL-3 independent cell lines are:

HMC-1, a factor-independent cell line derived from a patient with mast cell leukemia, expresses a juxtamembrane mutant c-kit polypeptide that has constitutive kinase activity (Furitsu T et al, J Clin Invest. 1993;92: 1736-1744; Butterfield et al, Establishment of an immature mast cell line from a patient with mast cell leukemia. Leuk Res. 1988;12:345-355 and Nagata et al, Proc Natl Acad Sci USA. 1995;92:10560-10564).

P815 cell line (mastocytoma naturally expressing c-kit mutation at the 814 position) has been described in Tsujimura et al, (1994), Blood 83, 2619-2626.

The extent to which component (ii) inhibits activated c-kit can be measured in vitro or in vivo. In case it is measured in vivo, cell lines expressing an activated-mutant c-kit, which has at least one mutation proximal to Y823, more particularly between amino acids 800 to 850 of SEQ ID No1 involved in c-kit autophosphorylation, notably the D816V, D816Y, D816F and D820G mutants, are preferred.

Example of cell lines expressing an activated-mutant c-kit are as mentioned.

In another preferred embodiment, the method further comprises the step consisting of testing and selecting compounds capable of inhibiting c-kit wild at concentration below 1 µM. This can be measured in vitro or in vivo.

In vivo testing may comprise measuring the ability of the tyrosine kinase inhibitors to alleviate arthritis symptoms in transgenic mouse model of arthritis that spontaneously develops a disease with many of the characteristics of rheumatoid arthritis in humans (Kouskoff et al., 1996 and U.S. Pat. No. 5,675,060). Alternatively, transgenic human TNF-a mouse model can be used.

Therefore, compounds are identified and selected according to the method described above are potent, selective and non-toxic c-kit wild inhibitors.

Alternatively, the screening method as defined above can be practiced in vitro. In this regard, the inhibition of mutant-activated c-kit and/or c-kit wild can be measured using standard biochemical techniques such as immunoprecipitation and western blot. Preferably, the amount of c-kit phosphorylation is measured.

In a still further embodiment, the invention contemplates a method for treating inflammatory diseases as depicted above wherein the screening comprises:

a) performing a proliferation assay with cells expressing a mutant c-kit (for example in the transphosphorylase domain), which mutant is a permanent activated c-kit, with a plurality of test compounds to identify a subset of candidate compounds targeting activated c-kit, each having an IC50<10 µM, by measuring the extent of cell death, b) performing a proliferation assay with cells expressing c-kit wild said subset of candidate compounds identified in step (a), said cells being IL-3 dependent cells cultured in presence of IL-3, to identify a subset of candidate compounds targeting specifically c-kit, c) performing a proliferation assay with cells expressing c-kit, with the subset of compounds identified in step b) and selecting a subset of candidate compounds targeting c-kit wild, each having an IC50<10 µM, preferably an IC50<1 µM, by measuring the extent of cell death.

Here, the extent of cell death can be measured by 3H thymidine incorporation, the trypan blue exclusion method or flow cytometry with propidium iodide. These are common techniques routinely practiced in the art.

The method according to the invention includes preventing, delaying the onset and/or treating inflammatory diseases in human.

Therefore, the invention embraces the use of the compounds defined above to manufacture a medicament for treating inflammatory diseases such as rheumatoid arthritis, conjunctivitis, rheumatoid spondylitis, osteoarthritis, gouty arthritis, polyarthritis, and other arthritic conditions as well as pain associated with these inflammatory diseases.

The pharmaceutical compositions utilized in this invention may be administered by any number of routes including, but not limited to oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical compositions suitable for use in the invention include compositions wherein c-kit inhibitors are contained in an effective amount to achieve the intended purpose. The determination of an effective dose is well within the capability of those skilled in the art. A therapeutically effective dose refers to that amount of active ingredient, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therpeutic effects is the therapeutic index, and it can be expressed as the ratio, LD50/ED50. Pharmaceutical compositions which exhibit large therapeutic indices are preferred. As mentioned above, a tyrosine kinase inhibitor and more particularly a c-kit inhibitor according to the invention is unable to promote death of IL-3 dependent cells cultured in presence of IL-3.

The invention also concerns a product comprising a tyrosine kinase inhibitor as defined above and at least one anti-inflammatory compound selected from the group consisting of acetylsalicylic acid (aspirin), ibuprofen, naproxen, and cox2 inhibitors.

Utility of the invention will further ensue from the detailed description below.

EXAMPLE 1

Use of 4-(4-méthylpipérazine-1-ylmethyl)-N-[4-methyl-3-[(4-pyridine-3-ylpyrimidine-2 yl)amino] phényl]-benzamide for treating arthritis.

Protocol Treatment

Figure 1B:
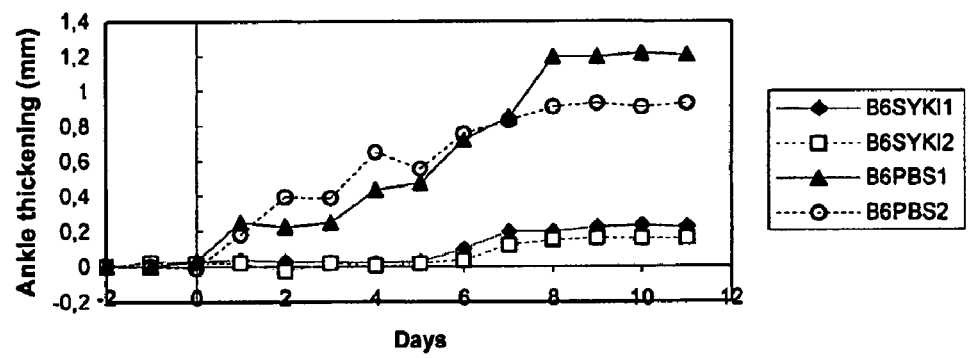
Figure 1C:
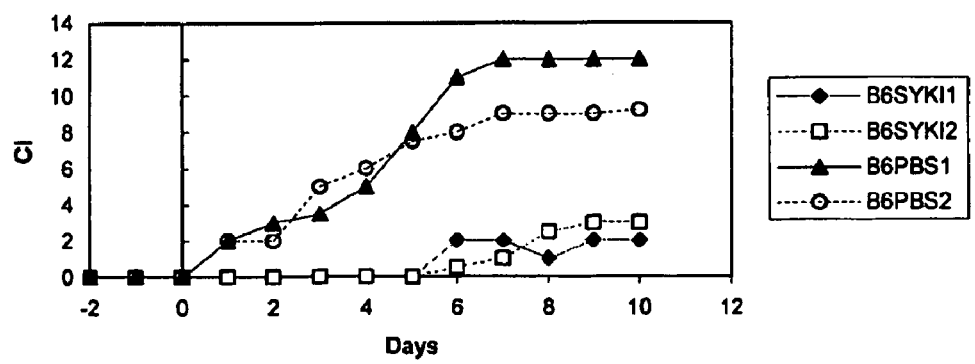
Figure 2A:
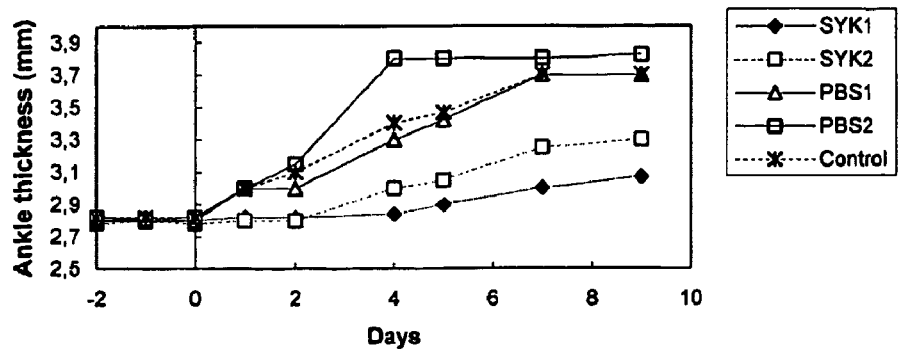
Figure 2B:
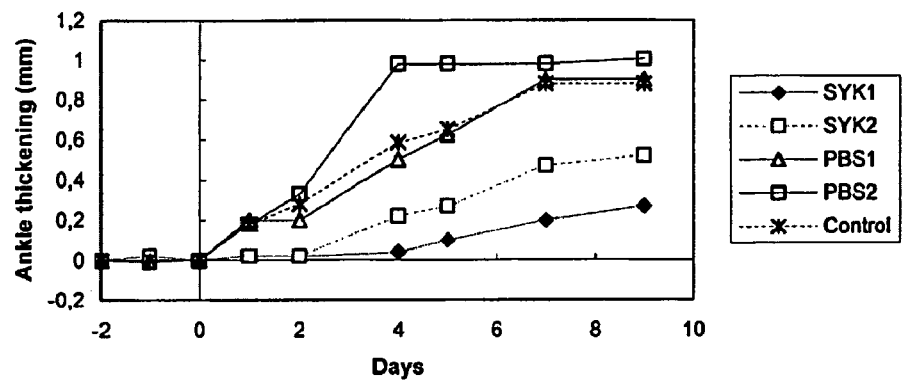
Figure 2C:
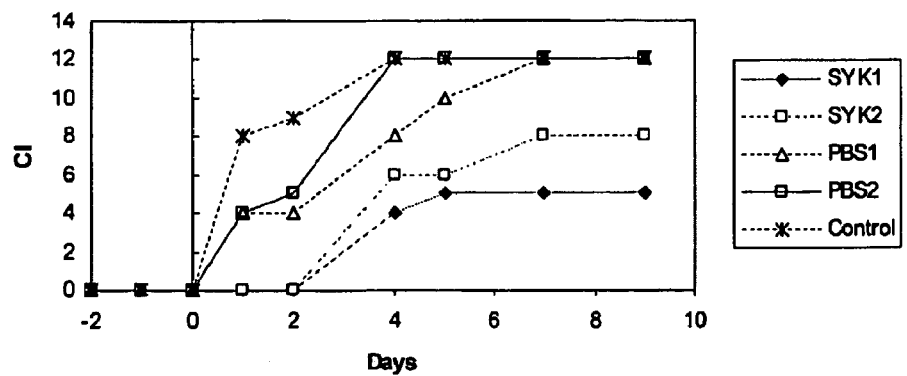

The mice were pretreated with the compound at different concentrations for two days (day-2, day-1) before induction of arthritis. Arthritis was induced by ip injection of 150 µl serum at days 0 and 2. The treatment with the compound at different concentration was continued during the course of the disease. The control mice were injected with acid PBS before the induction of arthritis and during the course of the disease. Ankle thickness and arthritis score was evaluated for 12 days. Arthritis Score: Sum of scores of each limb (0 no disease; 0.5 mild swelling of paw or of just a few digits; 1 clear joint inflammation; max score=4). The results are presented in FIGS. 1 and 2. Table 1 shows the number of mice used in this study.

TABLE 1

|  | BalbC/cj | C57Bl/6 |
|---|---|---|
| Compound concentration | | |
| 0.5 mg | 2 | |
| 1 mg | | 2 |
| 1.5 mg | | 2 |
| 2 mg | | |
| 3 mg | 2 | |
| Controls of the treated mice | | |
| 0.5 mg | 3 | |
| 1 mg | | 2 |
| 1.5 mg | | 2 |
| 2 mg | | |
| *3 mg | 2 | |

*The dose of 3 mg was lethal.

The compound was dissolved in acid PBS solution, pH 3. In order to rule out any toxic effect of this low pH studies on the natural activation of B and T cells was monitored. 3 mice were injected with acid PBS for 4 days and compared to 3 control mice that were injected with PBS.

Histology

At the end of the experiment the hind limbs were collected. The skin of the limb was removed and the limbs were subsequently fixed in 2% paraformaldehyde.

The invention claimed is:

1. A method for treating inflammatory diseases selected from the group consisting of rheumatoid arthritis, conjunctivitis, rheumatoid spondylitis, osteoarthritis, gouty arthritis, and polyarthritis, said method comprising administering an effective amount of the following compound:

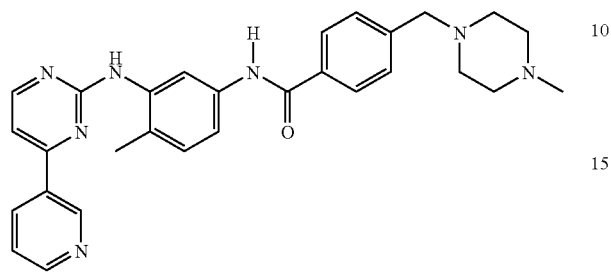

N-(3-(4-(pyridin-3-yl)pyrimidin-2-ylamino)-4-methylphenyl)-4-((4-methylpiperazin-1-yl)methyl)benzamide to a mammal in need of such treatment.

* * * * *